(12) United States Patent
Mackey et al.

(10) Patent No.: US 7,591,189 B2
(45) Date of Patent: Sep. 22, 2009

(54) GLASS TESTING APPARATUS

(75) Inventors: Randy L. Mackey, Bend, OR (US);
Christopher M. Boyle, Bend, OR (US);
Michael P. Boyle, Bend, OR (US)

(73) Assignee: Glas-Weld Systems, Inc., Bend, OR (US)

( * ) Notice: Subject to any disclaimer, the term of this patent is extended or adjusted under 35 U.S.C. 154(b) by 0 days.

(21) Appl. No.: 12/051,540

(22) Filed: Mar. 19, 2008

(65) Prior Publication Data

US 2008/0229844 A1    Sep. 25, 2008

Related U.S. Application Data

(60) Provisional application No. 60/919,280, filed on Mar. 20, 2007.

(51) Int. Cl.
*G01N 3/02* (2006.01)

(52) U.S. Cl. .......................................... 73/852; 73/856

(58) Field of Classification Search ............ 73/760–860
See application file for complete search history.

(56) References Cited

U.S. PATENT DOCUMENTS

| | | | | |
|---|---|---|---|---|
| 4,363,649 A * | 12/1982 | Yamato et al. | ................. | 65/158 |
| 4,395,917 A * | 8/1983 | Maltby et al. | ................. | 73/840 |
| 4,711,654 A * | 12/1987 | Iida | ............................ | 65/172 |
| 5,287,727 A * | 2/1994 | Nickerson, Jr. | ................. | 73/37 |
| 2002/0081189 A1 * | 6/2002 | Giometti | .................. | 414/791.2 |

* cited by examiner

*Primary Examiner*—Max Noori
(74) *Attorney, Agent, or Firm*—Schwabe, Williamson & Wyatt

(57) ABSTRACT

Embodiments of the present invention provide methods and apparatuses for testing the structural integrity of glass. Embodiments of the present invention provide a method and apparatus for testing glass by applying one or more stresses to the glass in a controlled manner. Embodiments of the invention may hold a sheet of glass and may subject the glass to a variety of stresses by flexing, twisting, vibrating, etc.

24 Claims, 2 Drawing Sheets

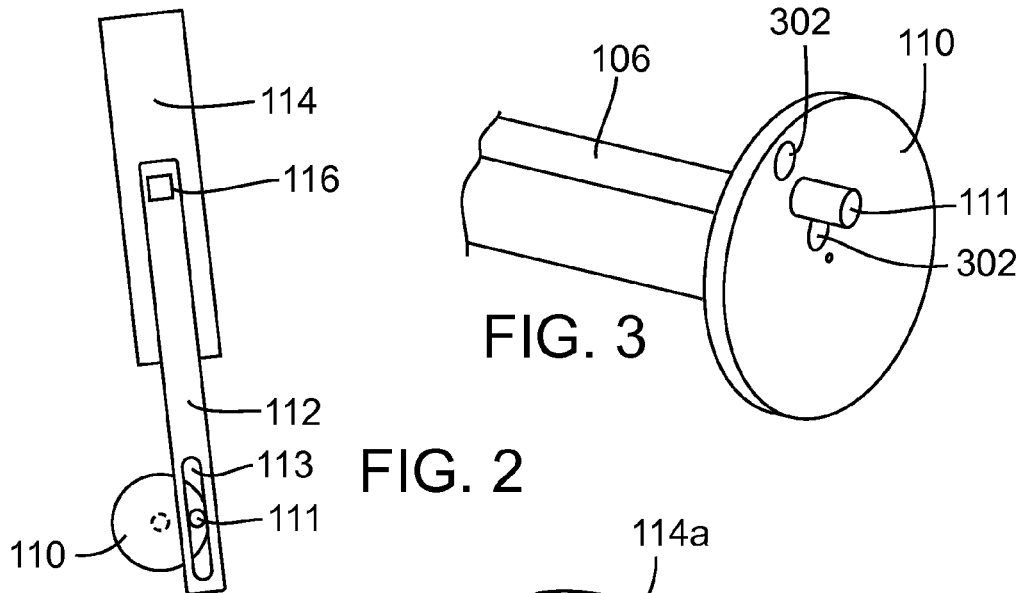
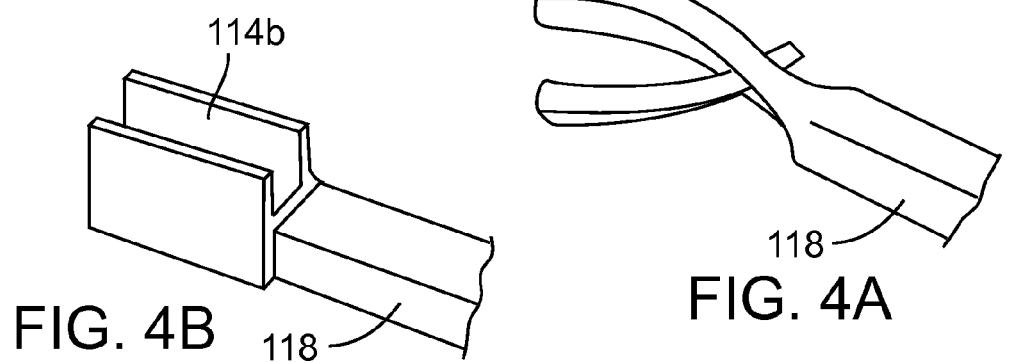
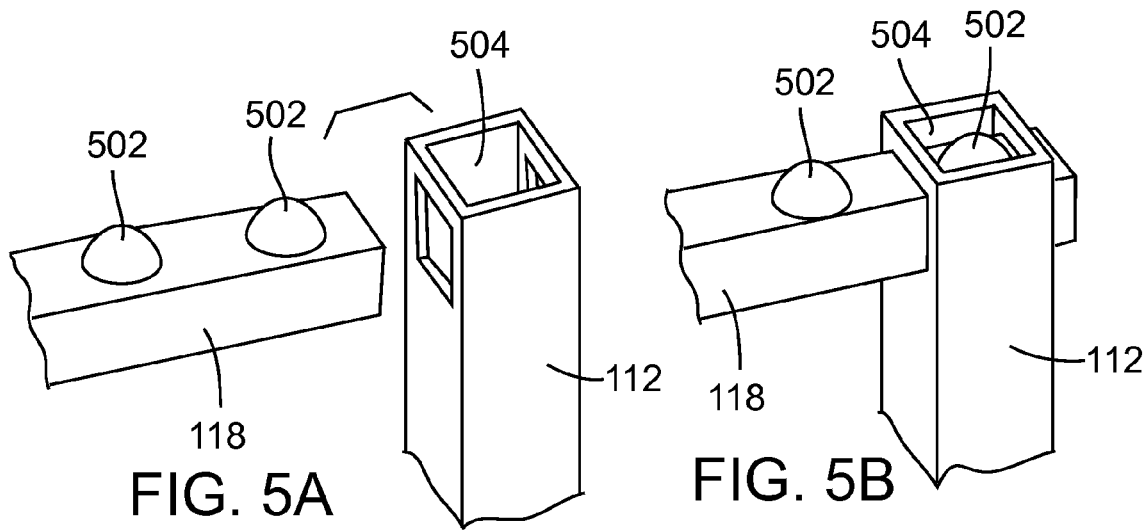

GLASS TESTING APPARATUS

CROSS REFERENCE TO RELATED APPLICATIONS

The present application claims priority to U.S. Provisional Patent Application No. 60/919,280, filed Mar. 20, 2007, entitled "Laminated Glass Testing Apparatus," the entire disclosure of which is hereby incorporated by reference in its entirety.

TECHNICAL FIELD

Embodiments of the present invention relate to a glass testing apparatus, and, more specifically, to an apparatus for testing glass to determine the structural integrity of glass subjected to stress.

BACKGROUND

The structural integrity of glass, such as a glass windshield, whether in a new, manufactured form or having been repaired, is important to the durability and longevity of the glass. Glass may encounter a variety of stresses caused by temperature, wind, vibration, snow, hail, debris, etc. that may break or damage the glass, especially if structural deficiencies are present.

With respect to repair of glass, such as glass windshields, there are many products currently available. However, one challenge in repairing glass, such as a windshield, is determining whether the repaired item is structurally sound. A similar concern exists for the testing of new glass elements. It is also difficult to ascertain the differences among the many repair methods or products, such as which methods or products are capable of restoring a piece of glass, such as a windshield, to a structurally sound condition.

Attempts have been made to provide testing guidelines for structural testing of glass, for example, by implementing testing procedures, notably tests from the ANSI Standard "ANSI Z26.1-1996" which is designed for testing new windshields which must pass this standard to be installed into an automobile in the USA. Another testing procedure for windshields is noted in the "Australian/New Zealand Standard (AS/NZS) 2366.2:1999" which is also adopted from a standard for testing new windshields.

These testing standards, however, fail to adequately test glass in a manner that is consistent with the actual stresses that the glass is subjected to, such as the stresses a windshield encounters while installed in a vehicle and while the vehicle is in operation.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

FIG. 2 illustrates a side view of part of a glass testing apparatus in accordance with various embodiments of the present invention;

FIG. 3 illustrates an exemplary adjustable cam in accordance with various embodiments of the present invention;

FIGS. 4A and 4B illustrate alternate holding arm clamps in accordance with various embodiments of the present invention; and FIGS. 5A and 5B illustrate an exemplary mechanism to control the spacing between glass holding arms in accordance with various embodiments of the present invention.

DETAILED DESCRIPTION OF EMBODIMENTS OF THE INVENTION

Figure 1:
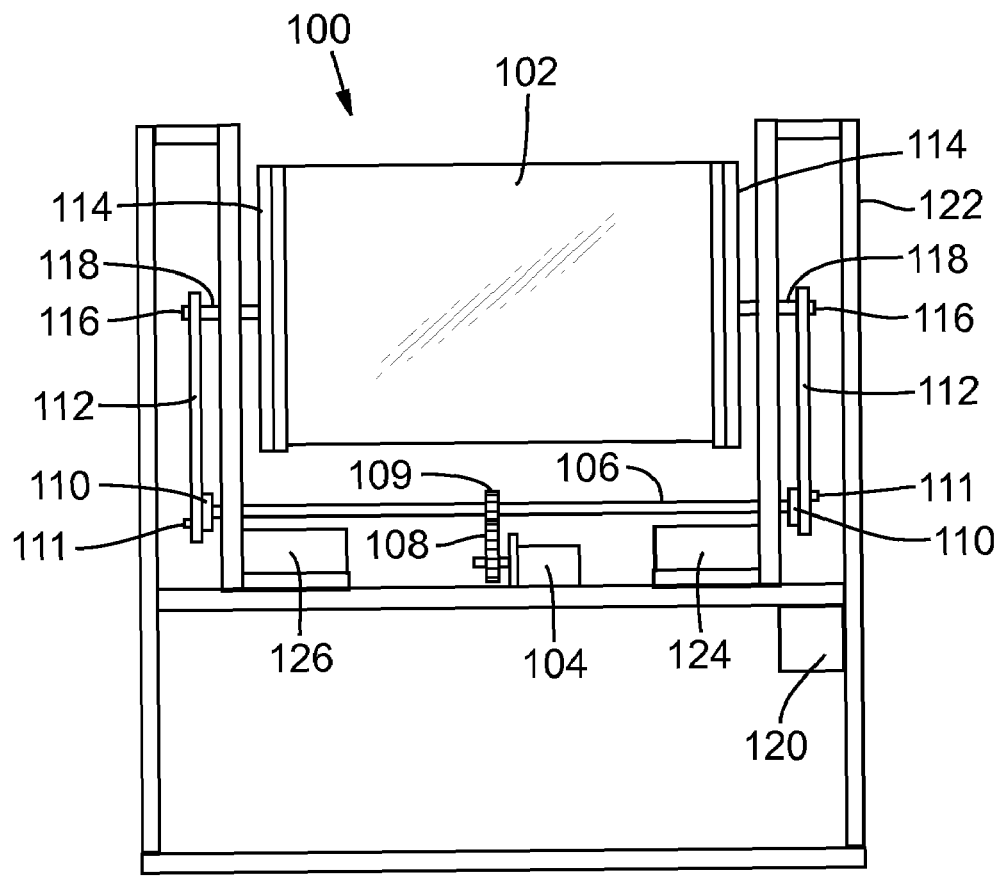
FIG. 1 illustrates a front view of a glass testing apparatus in accordance with various embodiments of the present invention.

In the following detailed description, reference is made to the accompanying drawings which form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. These terms may be synonymous and mean that two or more elements are in direct physical or electrical contact, or that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In various embodiments of the present invention, methods and apparatuses for testing the structural integrity of glass are provided.

Embodiments of the present invention provide a method and apparatus for testing glass by applying one or more stresses to the glass in a controlled manner. Embodiments of the invention may hold a sheet of glass and subject the glass to one or more of a variety of stresses, such as by flexing (including twisting), vibrating, impacting, heating and/or cooling the glass.

In an embodiment, there is provided a driver, such as a manually operable element, for example a hand crank, or a motor, for example an electric motor, to induce a force to articulate (i.e., move in one or more directions) the glass to induce stress to test the structural integrity of the glass. In various embodiments, the driver may be a direct drive motor with an electronic speed controller to control the stressing of the glass.

In an embodiment using a motor, there may be provided a gear system for the motor to induce a force to flex the tested glass in a controlled manner to simulate various stresses, such as the stress experienced by a windshield in a moving vehicle.

In an embodiment, there are provided articulating arms configured to hold a sheet of glass and to articulate the glass in different directions, such as articulating the opposing edges of the glass in opposing directions by flexing or twisting, to induce a stress on the glass.

In an embodiment, there is provided a rotating shaft coupled to a driver to impart rotation to the shaft. In an embodiment, the rotating shaft may be further coupled to articulating arms by members actuated by concentric cam action to convert rotational force (provided, for example, by a motor) into articulating force.

In an embodiment, a control switch may be provided coupled to a power source to switch on and switch off a motor, if a motor is utilized. In an embodiment, a motor may be provided with a variable speed controller to increase or decrease the speed of articulation of the glass. In another embodiment, a variable speed motor may be provided with an off center weight or other mechanism coupled to the apparatus to induce vibration to the glass simulating environmental vibration experienced by the glass. In an embodiment, such a variable speed motor may have the ability to vary the frequency of vibration by varying the speed of the motor.

In an embodiment, a separate vibratory element may be provided in or coupled to the testing apparatus at one or more of a variety of locations to cause the tested glass to vibrate to simulate vibration stress in conjunction with or separate from one or more other stresses. In an embodiment, a heating and/or cooling device (such as a heat sink) may be provided in or coupled to the testing apparatus to impart a heating/cooling effect on the tested glass to simulate heating/cooling stress in conjunction with or separate from one or more other stresses. In an embodiment, a striking element (hammer, mallet, striking ball, etc.) may be provided in the testing apparatus to impart an impact stress on the tested glass in conjunction with or separate from one or more other stresses.

Thus, in an embodiment, there is provided an apparatus for testing the structural integrity of glass, comprising a plurality of holding arms configured to form a space for the glass between the plurality of holding arms, each of the plurality of holding arms configured to hold at least part of the glass; a plurality of connectors or connecting members, the plurality of connecting members coupled to the plurality of holding arms, the plurality of connecting members configured to impart an articulating force on the plurality of holding arms to impart an articulating stress on the glass; and a driver coupled to the plurality of connecting members to provide the articulating force to the plurality of holding arms. In various embodiments, a polariscope may be used during the stressing process to identify where particular stresses are manifested in the glass.

For the purposes of describing embodiments of the present invention, the phrase "structural integrity" refers to the strength and durability of an element, such as when subjected to stress. Unacceptable structural integrity of a sheet of glass may be seen during and/or after testing if the glass cracks, chips, breaks, improperly flexes, etc.

For the purposes of describing embodiments of the present invention, the term "stress" refers to an environmental influences or external impacts that may be imparted on a sheet of glass to test the structural integrity of the glass. In various embodiments, a stress may be imparted, for example, by flexing, twisting, vibrating, heating/cooling, striking, etc. the glass.

For the purposes of describing embodiments of the present invention, the phrase "articulating stress" refers to a stress caused by manipulating glass, such as by flexing, twisting, etc.

Embodiments of the present invention may be used to test a variety of types of glass intended for different purposes. In an embodiment, methods and apparatuses may be used to test glass windshields intended for vehicles. For the purposes of describing embodiments of the present invention, the term "vehicle" is intended to be used broadly to refer to any device of conveyance that uses or may use a windshield, including cars, trucks, airplanes, boats, personal watercraft, recreational vehicles, etc.

While embodiments of the present invention are generally described with reference to testing the structural integrity of a windshield, it should be appreciated that use for testing glass, in general, is contemplated. In particular, an embodiment of the present invention may be used to test any suitable type of glass, such as tempered glass, laminated glass, insulated glass, safety glass, vehicle glass, etc. Embodiments of the present invention may be used to test the structural integrity of newly manufactured or repaired glass, as desired.

Glass that may be tested using embodiments of the invention may be flat or curved, may be uniform or non-uniform in shape/configuration, and may have any suitable thickness or thicknesses. Embodiments of the present invention may be configured for use with a specific shape(s) or size(s) of glass (length, width, thickness, etc.), or embodiments may be adjustable to allow for use with a variety of shapes and/or sizes.

FIG. 1 is a front view of a glass testing apparatus 100 for testing the structural integrity of glass 102 when subjected to added stress, for example, due to flexing. FIG. 2 is a partial side view of apparatus 100. In an embodiment, an electric motor 104 may be used to induce rotational force to the rotating shaft 106 through a gear system 108, 109 to provide a controlled rotational speed. In embodiments, any suitable gear ratio may be selected for gears 108, 109, and, in embodiments, more or less gears may be used. In embodiments, other types of motors may be used, such as electrostatic, pneumatic, hydraulic, etc. In other embodiments, manually operable drivers, such as a hand crank, may be used.

In an embodiment, rotational force may be transmitted from motor 104 through gear 108 to gear 109. The rotation of gear 109 causes rotating shaft 106 to transmit rotational force to cams 110 which further convert the rotational force to a reciprocating force. As shown in FIG. 1, cams 110 may be oriented differently to impart different forces to each of connecting members 112 when rotating shaft 106 causes cams 110 to rotate. In embodiments, cam pins 111 on each of cams 110 may be aligned with each other or may be differently oriented (i.e., configured with different timing) to impart the induced force(s) on glass 102. In an embodiment, cam pins 111 may be configured to engage with corresponding slots 113 on connecting members 112.

In embodiments, different sizes of cams 110 may be utilized to impact the extent of articulation of holding arms 114. In an embodiment, cams 110 may be provided with cam pins 111 that are adjustable to vary the distance of cam pins 111 from the center of cam 110. For a given cam 110, the greater radial distance from the center of cam 110 at which cam pin 111 is placed, the greater articulation that will be imparted on holding arms 114 and thus on glass 102. In an embodiment, depending on the innate flexibility of glass 102 or the desired flex testing parameters, more or less articulation may be desired. As such, FIG. 3 shows a cam 110 with cam pin 111 and various holes 302 for placement of cam pin 111.

In an embodiment, connecting members 112 transmit the reciprocating force to glass holding arms 114. Glass holding arms 114 are used to hold a sheet of glass 102 that is being tested. In an embodiment, glass holding arms 114 may have a variety of holding mechanisms, such as clamps, channels, etc. to secure glass 102 between holding arms 114. In an embodiment, a clamp or channel may be open at the top and bottom, open at the top or bottom, or closed at both the top and bottom, in each case forming a region for an edge of the glass to reside during testing. Glass holding arms 114 may hold an edge of glass 102 completely or may only contact a portion of an edge of glass 102, such as with a smaller clamp, such as clamps 114a and 114b shown in FIGS. 4A and 4B.

In an embodiment, glass holding arms 114 may be provided with threaded knobs 116 or other suitable mechanism to control the spacing between holding arms 114. In an embodiment, threaded knobs 116 may be tightened to decrease the space between holding arms 114 or loosened to increase the space. In various embodiments, spacers may be used to control the spacing.

In an embodiment, intermediate bars 118 of holding arms 114 may couple to connecting members 112 such that movement of connecting member 112 translates into movement of bar 118. In an embodiment, bars 118 of holding arms 114 may couple to connecting members 112 at a number of locations, such as a number of preset locations, for example, as shown in FIGS. 5A and 5B, by interaction of one or more spring loaded pins 502 and one or more holes 504, to control the spacing between holding arms 114. FIG. 5A illustrates the disengaged relationship between bar 118 and connecting member 112, while FIG. 5B illustrates an engaged relationship. In FIG. 5B, the first spring loaded pin 502 is engaged with hole 504. Alternative arrangements may also be utilized in embodiments, such as the locations of pins 502 and holes 504 being reversed, or different mating or engagement systems as desired.

In an embodiment, glass 102 may be held between glass holding arms 114 on each of two opposite edges of glass 102. In an embodiment, by operating motor 104 to turn rotating shaft 106, glass 102 may be subjected to articulating stress caused by articulating each glass holding arm 114 in a direction different from the other.

In an embodiment, a control switch 120 may be provided to easily control the operation of motor 104. Switch 120 may be any suitable switch, such as a simple on/off switch, a multi-position switch, etc. to control the use of power and/or to control other selected function(s) of apparatus 100 (vibration, heating/cooling, etc.).

In an embodiment, a framework 122 may be used to hold the features of apparatus 100 together and to provide a support for the various structures. Framework 122 may be constructed from one or more of a variety of materials, including metals, alloys, plastics, wood, etc.

In various embodiments, additional stress inducing mechanisms may be provided with or without a flex inducing device. In an embodiment, a vibratory element 124 may be provided in or coupled to apparatus 100 to cause the tested glass to vibrate to simulate vibration stress in conjunction with or separate from one or more other stresses. In an embodiment, a heating and/or cooling device 126 (such as a heat sink) may be provided in or coupled to apparatus 100 to impart a heating and/or cooling effect on the tested glass to simulate heating and/or cooling stress in conjunction with or separate from one or more other stresses.

Methods of use of embodiments of the invention are also provided. In an embodiment, a method for testing the structural integrity of glass, comprising placing the glass in an apparatus to hold the glass, the apparatus comprising a plurality of holding arms configured to form a space for the glass between the plurality of holding arms, each of the plurality of holding arms configured to hold at least part of the glass, a plurality of connecting members, the plurality of connecting members coupled to the plurality of holding arms, the plurality of connecting members configured to impart an articulating force on the plurality of holding arms to impart an articulating stress on the glass, and a driver coupled to the plurality of connecting members to provide the articulating force to the plurality of holding arms, and subjecting the glass to an articulating stress to determine the structural integrity of the glass.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. An apparatus for testing the structural integrity of glass, comprising:
    a plurality of holding arms configured to form a space for the glass between the plurality of holding arms, each of the plurality of holding arms configured to hold at least part of the glass;
    a plurality of connectors coupled to the plurality of holding arms, the plurality of connectors configured to impart an articulating force on the plurality of holding arms to impart an articulating stress on the glass, wherein the articulating force comprises at least one of twisting and flexing the glass; and
    a driver coupled to the plurality of connectors to provide the articulating force to the plurality of holding arms.

2. The apparatus of claim 1, wherein each of the plurality of holding arms comprises at least one of a clamp and a channel to engage with the glass.

3. The apparatus of claim 1, wherein each connector is coupled to a holding arm by an intermediate bar.

4. The apparatus of claim 3, wherein each intermediate bar is adjustably coupled to the connector and/or a holding arm to adjust the space between the holding arms.

5. The apparatus of claim 1, wherein the driver is coupled to a shaft to provide rotational force to the shaft, the shaft is coupled at each end to a cam, and the cams are coupled to the connectors to translate rotational force provided by the driver to a reciprocating force provided to the connectors.

6. The apparatus of claim 5, wherein the driver is coupled to the shaft by operation of a gear system, the driver comprising a first gear and the shaft comprising a second gear, rotation of the first gear causing rotation of the second gear and associated rotation of the shaft.

7. The apparatus of claim 5, wherein each of the cams comprises a cam pin for engaging with a corresponding slot on an associated connector.

8. The apparatus of claim 7, wherein the cams each have a plurality of locations for placement of the cam pins.

9. The apparatus of claim 5, wherein the cams comprise a first cam having a first cam pin and a second cam having a second cam pin, the first cam pin being configured with a different timing from a configuration of the second cam pin.

10. The apparatus of claim 1, wherein the driver is manually operable.

11. The apparatus of claim 1, wherein the driver is a motor.

12. The apparatus of claim 11, wherein the motor is electric, electrostatic, pneumatic, or hydraulic.

13. The apparatus of claim 11, wherein the motor includes an integrated vibration inducing component for imparting a vibrational stress on the glass.

14. The apparatus of claim 1, further comprising a vibration inducing component for imparting a vibrational stress on the glass.

15. The apparatus of claim 1, further comprising a heating/cooling device for imparting a heating/cooling stress on the glass.

16. The apparatus of claim 1, further comprising a framework for supporting one or more components of the apparatus.

17. The apparatus of claim 1, wherein the holding arms are configured to hold a windshield.

18. The apparatus of claim 5, wherein the driver is a direct drive motor with an electronic speed control.

19. A method for testing the structural integrity of glass, comprising:
    placing the glass in an apparatus to hold the glass, the apparatus comprising:
        a plurality of holding arms configured to form a space for the glass between the plurality of holding arms, each of the plurality of holding arms configured to hold at least part of the glass;
        a plurality of connectors, the plurality of connectors coupled to the plurality of holding arms, the plurality of connectors configured to impart an articulating force on the plurality of holding arms to impart an articulating stress on the glass;
        a driver coupled to the plurality of connectors to provide the articulating force to the plurality of holding arms; and
    subjecting the glass to an articulating stress to determine the structural integrity of the glass, wherein the articulating stress is caused by at least one of twisting and flexing the glass.

20. The method of claim 19, further comprising viewing the glass through a polariscope and identifying locations of various stresses on the glass.

21. The method of claim 19, further comprising subjecting the glass to at least one of a vibrational stress, a heating/cooling stress, and an impact stress.

22. An apparatus for testing the structural integrity of glass, comprising:
    a plurality of holding arms configured to form a space for the glass between the plurality of holding arms, each of the plurality of holding arms configured to hold at least part of the glass;
    a plurality of connectors coupled to the plurality of holding arms, the plurality of connectors configured to impart an articulating force on the plurality of holding arms to impart an articulating stress on the glass;
    a driver coupled to the plurality of connectors to provide the articulating force to the plurality of holding arms; and
    a vibration inducing component for imparting a vibrational stress on the glass.

23. The apparatus of claim 22, wherein the vibration inducing component is an integrated component of the driver.

24. An apparatus for testing the structural integrity of glass, comprising:
    a plurality of holding arms configured to form a space for the glass between the plurality of holding arms, each of the plurality of holding arms configured to hold at least part of the glass;
    a plurality of connectors coupled to the plurality of holding arms, the plurality of connectors configured to impart an articulating force on the plurality of holding arms to impart an articulating stress on the glass;
    a driver coupled to the plurality of connectors to provide the articulating force to the plurality of holding arms; and
    a heating/cooling device for imparting a heating/cooling stress on the glass.

* * * * *